(12) United States Patent
Wu et al.

(10) Patent No.: US 9,198,894 B2
(45) Date of Patent: Dec. 1, 2015

(54) USES OF 15-BENZYLIDENE-14-DEOXY-11,12-DIDEHYDROANDROGRAPHOLIDE DERIVATIVES IN THE PREPARATION OF ANTINEOPLASTIC DRUGS

(75) Inventors: Fengjuan Wu, Zhengzhou (CN); Guifu Dai, Zhengzhou (CN); Haiwei Xu, Zhengzhou (CN); Zhiwen Jiang, Zhengzhou (CN); Liping Zhu, Zhengzhou (CN); Lijun Yan, Zhengzhou (CN); Hongmin Liu, Zhengzhou (CN); Yanan Wang, Zhengzhou (CN); Weiyi Li, Zhengzhou (CN); Ruijing Dong, Zhengzhou (CN)

(73) Assignee: Zhengzhou University, Zhengzhou, Henan Province (CN)

( * ) Notice: Subject to any disclaimer, the term of this patent is extended or adjusted under 35 U.S.C. 154(b) by 0 days.

(21) Appl. No.: 13/823,841

(22) PCT Filed: Oct. 19, 2011

(86) PCT No.: PCT/CN2011/080966
§ 371 (c)(1),
(2), (4) Date: May 8, 2013

(87) PCT Pub. No.: WO2012/051941
PCT Pub. Date: Apr. 26, 2012

(65) Prior Publication Data
US 2013/0237596 A1    Sep. 12, 2013

(30) Foreign Application Priority Data
Oct. 22, 2010  (CN) .......................... 2010 1 0516322

(51) Int. Cl.
*A61K 31/365*    (2006.01)
*C07D 307/33*    (2006.01)
*A61K 31/341*    (2006.01)
*A61K 45/06*    (2006.01)

(52) U.S. Cl.
CPC ............ *A61K 31/341* (2013.01); *A61K 31/365* (2013.01); *A61K 45/06* (2013.01); *C07D 307/33* (2013.01)

(58) Field of Classification Search
CPC ........................... A61K 31/365; C07D 307/33
USPC ........................................................ 514/473
See application file for complete search history.

(56) References Cited

U.S. PATENT DOCUMENTS
2010/0330197 A1 * 12/2010 Higashiguchi et al. ....... 424/638

FOREIGN PATENT DOCUMENTS
CN          1978437 A    *    6/2007

OTHER PUBLICATIONS

Dai et al. (Bioorganic & Medicinal Chemistry Letters 16 (2006) 2710-2713).*
Qu et al.—(Agric. Chem. Biotechnol. 49(4), 140-142 (2006)).*
Dai et al. CN1978437A . Jun. 2007. English Abstract.*
Sporn et al. "Chemoprevention of Cancer". Carcinogenesis. 2000; 21 (3):525-530.*
Thoppil et al. "Terpenoids as Potential Chemopreventive and Therapeutic Agents in Liver Cancer". World J Hepatol. Sep. 27, 2011; 3(9):228-249.*
Costello et al. "Evidence for Changes in RREB-1, ZIP3, and Zinc in the Early Development of Pancreatic Adenocarcinoma". J Gastrointest Canc. 2012; 43:570-578.*
Martin et al. "Do Structurally Similar Molecules Have Similar Biological Activity?" Journal of Medicinal Chemistry. 2002; 45:4350-4358.*
Osol A. [Editor]. "Chapter 27: Structure-Activity Relationship and Drug Design". Remington's Pharmaceutical Sciences (Sixteenth Edition). Mack Publishing. 1980. pp. 420-435.*
Holliday et al. (Breast Cancer Research 2011, 13:215).*
Gennaro, Alfonso. (Remington's pharmaceutical Sciences. Easton, PA:Mack Pub. Co., 1990).*

* cited by examiner

*Primary Examiner* — Jeffrey S Lundgren
*Assistant Examiner* — Chris Simmons
(74) *Attorney, Agent, or Firm* — Blank Rome LLP (57) ABSTRACT

The present invention relates to the preparation of anti-tumor drugs with andrographolide derivatives, which belongs to the field of pharmaceutical technology, and involves 15-benzylidene substituted derivatives of 14-deoxy-11,12-didehydro-andrographolide and their 3,19-ester derivatives. Proved by the experiments, these compounds significantly inhibited the colony formation and migration ability of various cancer cells, and also inhibited the migration ability of vascular endothelial cells in vitro. The compounds of this invention significantly inhibited the tumor growth, invasion, metastasis and angiogenesis on mouse xenograft models, and inhibited the experimental lung metastasis of B16-F10 malignant melanoma cells. Therefore, this class of compounds could be used as the active ingredients for the preparation of antineoplastic drugs, which are of efficiency and low-toxicity. Thereby it has potential to expand the selectable range of clinical drug and is of high significance to make full use of the plant resources of *Andrographis paniculata*.

10 Claims, 3 Drawing Sheets

USES OF 15-BENZYLIDENE-14-DEOXY-11,12-DIDEHYDROANDROGRAPHOLIDE DERIVATIVES IN THE PREPARATION OF ANTINEOPLASTIC DRUGS

FIELD OF THE INVENTION

The present invention relates to the pharmaceutical use of andrographolide derivatives, which belongs to the field of pharmaceutical technology. Among these derivatives, 15-benzylidene substituted derivatives of 14-deoxy-11,12-didehydro-andrographolide and their 3,19-ester derivatives are included.

BACKGROUND OF THE INVENTION

In recent years, due to the increasing competition in modern society, the increased life stress, more and more serious environment pollution and so on, the morbidity and mortality of malignant tumor are higher than ever before, which makes tumor the second leading cause of death. Therefore, it is of high significance to develop drugs for the treatment of tumor.

Andrographolide (AD), a kind of diterpene lactone compounds extracted from *Andrographis paniculata* (Burm. f.) Nees which has long been widely used as a folk remedy to alleviate inflammatory disorders in Asia exhibits multiple pharmacological activities. It can be used for the treatment of various ailments, including fever, inflammation, bacterial dysentery, viral infection, tumor, etc. As for the anti-tumor effect, present studies are mainly focused on improving the cytotoxic activity by structural modification or clarifying the mechanism of apoptosis induced by AD. Dr. Reddy's Laboratories LTD has applied for a patent entitled "Preparation and antitumor activity of andrographolide derivs" (WO 2001057026; CN 1416428) to protect the applications of some andrographoide derivatives to the treatment of cancer, infections of HSV or HIV, or psoriasis. The First Affiliated Hospital of Peking University has disclosed the inhibitory effect of diterpene lactone compounds from *Andrographis paniculata* on angiogenesis in the patent (CN 1511522). A patent applied by Henan University, "A drug combination containing isoandrographolide and its medical uses" (CN 1785177), relates to a drug combination which takes isoandrographolide as the active component containing the pharmaceutically acceptable carrier and its use in the preparation of anti-inflammatory or anti-tumor drugs. A patent applied by Guang Han, "A drug combination containing 3, 14, 19-triacetyl-andrographolide and its medical uses" (CN 101129354), relates to a drug combination which takes 3, 14, 19-triacetyl-andrographolide as the active component containing pharmaceutically acceptable carrier and its use in the preparation of anti-inflammation, immunosuppression and anti-tumor drugs. Hutchison MediPharma Limited has applied for a patent, entitled "the medicinal use of andrographolide, its derivatives and analogs" (CN 1666985), which involves the use of this kind of compounds or their prodrugs in the preparation of TNF-α and/or IL-1β inhibitor.

Indian scientists Nanduri and others synthesized nearly 100 kinds of derivatives by modifying andrographolide at the hydroxyls of C-3, C-14, C-19, and confirmed that these compounds had obvious inhibitory effects on the proliferation of a variety of human cancer cells in vitro, such as MCF-7 breast cancer, SW-620 and HT-29 colon cancer, H522 lung cancer, UACC62 and M14 melanoma, SKOV-3, OVCAR and PA1 ovarian cancer, DU145 and PC-3 prostate cancer, and A498 and ACHN renal cell carcinoma. Showed by the research of Srinivas, et al., the exocyclic $\Delta^{8(17)}$ double bond of andrographolide may not play any important role and can be replaced with an epoxy moiety, and then the cytotoxicity significantly improved when further convert these derivatives to esters. Xinyang Wang, et al., synthesized 21 new isoandrographolide dioxalyl esters or dioxalyl amides, and found that 3,19-di{(n-butylamine) carbonyl carboxyl}-O-isoandrographolide was to possess similar antitumor activity and better chemical stability to andrographolide through assay the cytotoxicity by MTT method. Hao Xu, et al., synthesized N-acetyl-12-aminomethyl-14-deoxy andrographolide derivatives (4a-4j) and then appraised the anti-tumor activity of them, and confirmed that all of the ten compounds showed cytotoxicity against BGC823 and SGC-7901 human gastric adenocarcinoma cells and SMMC7721 human hepatoma cells in different levels. The inhibitory effect of compound 4c on SMMC7721 hepatocellular carcinoma is stronger than that of andrographolide, which is similar to that of cisplatin.

However, the structure modifications above were mainly performed at the hydroxyls of C-3, C-14, C-19, and the double bond of $\Delta^8, \Delta^{12}$, etc. It is of great significance for the application of these compounds and for the protection of our independent intellectual property rights to study the antitumor effect of the C15-substituted analogues of andrographolide.

SUMMARY OF THE INVENTION

The present inventors have designed and synthesized more than one hundred compounds with novel structures (CN 1978437; CN 100999520; CN 100999535; CN 101003527). Further studies showed that some 15-benzylidene substituted derivatives of 14-deoxy-11,12-didehydro-andrographolide had much better anti-tumor activity than andrographolide. The aim of the invention is to apply 15-benzylidene substituted derivatives of 14-deoxy-11,12-didehydro-andrographolide and their 3,19-ester derivatives to antineoplastic drug application.

Compounds of the invention have the structure of formula 1: wherein $R_1$ is hydrogen; $R_2$ is phenyl, p-methoxyphenyl or p-halophenyl; $R_3$ and $R_4$ are each independently hydrogen or $COR_5$, of which $R_5$ is 3-pyridyl or $CH_2CH_2COOH$.

Formula 1

Preferred compounds of this invention are those wherein $R_1$ is hydrogen; $R_2$ is phenyl, p-methoxyphenyl, p-fluorophenyl, p-chlorophenyl, p-bromophenyl, 3-fluorophenyl, 3-chlorophenyl or 3-bromophenyl; $R_3$ and $R_4$ are both hydrogen.

Preferred compounds of this invention also are those wherein $R_1$ is hydrogen; $R_2$ is phenyl, p-methoxyphenyl, p-fluorophenyl, p-chlorophenyl, p-bromophenyl, 3-fluorophenyl, 3-chlorophenyl or 3-bromophenyl; $R_3$ and $R_4$ are both $COR_5$, of which $R_5$ is 3-pyridine or —$CH_2CH_2COOH$.

The preparation method used to synthesize the compounds of this invention has been made public in the previous patent CN 200510107247.4, which is as follows in brief:

One of the 14-deoxy-11,12-dehydro-andrographolide or 3,19-ester derivatives of 14-deoxy-11,12-dehydro-andrographolide and a kind of aldehydes were dissolved in methanol, ethanol or tetrahydrofuran, and then the andrographolide derivatives showed in Formula 1 can be obtained through heating the mixture at the temperature of 15 to 70, catalyzing by base at 0.2 to 5% (mol/mol). Wherein the base used is one of sodium carbonate, potassium carbonate, potassium bicarbonate, sodium bicarbonate, triethylamine, pyridine and N,N-dimethylamino pyridine.

The aldehydes used are one of the aromatic aldehydes; the optimized are benzaldehyde and halogenated benzaldehydes, and so on; the further optimized are benzaldehyde, p-fluoro-, p-chloro- and p-bromo-benzaldehyde, and p-methoxybenzaldehyde. The ester derivatives of 14-deoxy-11,12-dehydro-andro-grapholide used are those when $R_3$ and $R_4$ in formula 1 are both $COR_5$, of which $R_5$ is 3-pyridine or —$CH_2CH_2COOH$.

To achieve the objects of the present invention, the colony formation assay was used to determine the inhibitory effects of compounds on the clone formation ability of various tumor cells; the wound healing assay was performed to study the inhibitory effects of the compounds on tumor cell migration; wound healing and Transwell chamber assays were used to investigate the inhibitory effects of the compounds on the migration of human ECV304 vascular endothelial cells. And then, models of mouse H22 xenograft tumor and S180 sarcoma were established to study the anti-tumor and anti-angiogenic effects of compounds 2 and 3. Experimental lung metastasis model of mouse melanoma B16-F10 cells in C57BL/6 mice was used to study the anti-metastatic role of the compounds. Besides, the cytotoxicity of compounds were appraised by using compounds 2 and 3 as examples to explore the oral toxicity in mice with single dose acute toxicity test. Results showed that the compounds of this invention have anti-tumor effect, and low toxicity but high effectiveness, which could be used as the active ingredients to prepare drugs for treatment of gastric cancer, lung cancer, cervical cancer, bladder cancer, esophageal cancer, colon cancer, liver cancer, prostate cancer and melanoma.

According to the requirements for conventional pharmaceutical methods and process, the compounds are used as the effective medicinal ingredients or combined with other drugs, mixed with any auxiliary and/or added ingredients acceptable in pharmacy, to prepare anti-tumor drugs, including oral preparations and injections. The oral preparations include tablets, pills, capsules, granules and syrups; while injections include injectable solutions and lyophilized powder for injection.

The advantages of the present invention include: these compounds are of high anti-tumor activity, and are of high efficiency and low toxicity, and can be used as the active pharmaceutical ingredients for the development of anti-cancer drugs, which would provide novel drugs for the prevention and treatment of tumor metastasis, and also be of significance for the full use of the plant resources of *Andrographis paniculata*.

DETAILED DESCRIPTION OF THE INVENTION

With pharmacological test, the andrographolide derivatives 2-8, especially the 15-p-chlorobenzylidene-14-deoxy-11,12-didehydro-andrographolide (compound 2) and 15-p-chlorobenzylidene-14-deoxy-11,12-didehydro-3,19-dinicotinate andrographolide (compound 3), are used as the examples to illustrate the anti-tumor activity in detail.

Example 1

Inhibition of Tumor Cell Colony Formation by Compounds of the Present Invention 1.1 Materials and Methods 1) Cell lines: Cell lines of SGC-7901 human gastric cancer, A549 human lung adenocarcinoma and Hela human cervical carcinoma were purchased from the Type Culture Collection of the Chinese Academy of Sciences, Shanghai, China.

2) Culture medium and other materials: RPMI1640 medium, high glucose DMEM and trypsin were the products of Gibico Invitrogen Coperation. Fetal bovine serum (standard) was obtained from Tianjin Haoyang Biological Products Technology Co., Ltd., China. Fetal calf serum (FCS) was purchased from Hangzhou Sijiqing Biological Engineering Materials Co., Ltd., China. Andrographolide (1) was obtained from Furen Medicines Group, Pharmaceutical Co., Ltd., China. Andrographolide derivatives were synthesized by the New Drug Research & Development Center of Zhengzhou University, China. 6-well microtitre plates were purchased from Corning Costar (Lowell, Mass., USA).

3) Method: Colony formation assay was used. The cells were trypsinized to generate a single-cell suspension and seeded in a 6-well plate at a density of 100 cells/well, then drug-containing medium was added to the well to make the final concentration of compound to 0, 1.25, 2.50, 5.00, 7.50, 10.00 µmol/L, respectively. The experiments were performed in duplicate, and the cells were cultured at 37 in a humidified atmosphere with 5% $CO_2$. Terminate cell culture when the clones can be seen in the culture plate, then remove the culture medium, and wash twice with PBS, fix the cells with methanol (5 ml/well) for 15 min and stain the cells with hematoxylin-eosin stain. The number of clones which comprised more than 50 cells was counted under a TS100-F-PH microscope (Nikon Company, Japan). Calculate relative colony formation ratio (%) and the $IC_{50}$ values. Relative colony formation ratio (%)=(colony number of drug-administration well/colony number of control well)×100%.

1.2 Results

The results of inhibitory activities against colony formation of A549, SGC-7901 and Hela cells by compounds of this invention were shown in Table 1. It indicated that the compounds were of significant inhibitory effect on colony formation of tumor cells. The inhibition of compounds 2, 5, 6 and 7 against A549, SGC-7901 and Hela, as well as compound 4 against A549 and SGC-7901 were remarkably stronger than that of andrographolide, respectively.

TABLE 1

Inhibition against tumor cell colony formation by compounds of this invention ($IC_{50}/\mu M$)

| | Cell lines | | |
|---|---|---|---|
| Compound | A549 | Hela | SGC-7901 |
| AD(1) | 11.28 | 2.91 | 19.00 |
| 2 | 1.42 | 1.38 | 2.10 |
| 4 | 4.51 | 4.84 | 5.07 |
| 5 | 2.27 | 1.47 | 2.07 |
| 6 | 1.67 | 1.98 | 2.63 |
| 7 | 3.31 | 2.40 | 2.45 |

Notes:
The compound structures are showed in formula 1, wherein 2: $R_1=H$, $R_2=4\text{-Cl}-C_6H_4$, $R_3=R_4=H$; 4: $R_1=H$, $R_2=C_6H_5$, $R_3=R_4=H$; 5: $R_1=H$, $R_2=4\text{-F}-C_6H_4$, $R_3=R_4=H$; 6: $R_1=H$, $R_2=4\text{-Br}-C_6H_4$, $R_3=R_4=H$; 7: $R_1=H$, $R_2=4\text{-CH}_3\text{O}-C_6H_4$, $R_3=R_4=H$.

Example 2

Inhibition of Tumor Cell Migration 2.1 Materials and Methods

1) Cell lines: Cell lines of 5637 human bladder carcinoma, Eca-109 human esophageal carcinoma, HT29 human colon cancer, SGC-7901 human gastric cancer, A549 human lung adenocarcinoma and PC-3 human prostate carcinoma were purchased from the Type Culture Collection of the Chinese Academy of Sciences, Shanghai, China.

2) Reagents and other materials: Culture medium and other materials are the same with EXAMPLE 1.

3) Methods: The cells were trypsinized to generate a single-cell suspension and seeded in 96-well plates (200 μl/well), and incubated with medium containing 10% fetal bovine serum at 37 in a humidified atmosphere with 5% $CO_2$. Following a 24 h incubation, the cells were starved for an additional 12 h in low-serum media (1% FBS). The cultures of Eca-109, HT29, 5637, SGC-7901, A549 and PC-3 were then scratched away with a 200-μl plastic pipette tip and rinsed twice with PBS to remove wound-derived loose and dislodged cells. The cells were cultured in replaced medium without or with compounds at final concentrations of 0, 2.50, 5.00 and 10.00 μmol/L, respectively. At least seven randomly selected views along the scraped line in each well were photographed immediately and 24 h and 36 h after incubation using a digital camera at 50× magnification. The average scraped area in each well under each treatment condition was measured, and the percentage of inhibition against cell migration was calculated. % of inhibition=$1-(A_0-A_t)/(A'_0-A'_t)\times 100\%$, where, $A_0$ and $A_t$ are the areas of wound with compound treatment measured immediately and 24 or 36 h post-injury, respectively; $A'_0$ and $A'_t$ are the areas of wound without compound treatment measured immediately and 24 or 36 h post-injury, respectively.

2.2 Results

As shown in FIG. 1, compounds of this invention had obvious inhibitory effects on migration of Eca-109, HT29, 5637, SGC-7901, A549 and PC-3 tumor cells; in which the inhibitions of 5637 and SGC-7901 by compound 2, the inhibitions of A549 and Eca-109 by compound 3, 5 or 8, as well as the inhibitions of 5637 and PC-3 by compound 4 were much stronger than that of other tumor cells. Similar to andrographolide, compound 7 had stronger inhibition against migration of 5637 and A549 cells.

(Notes for FIG. 1: Results were those when cells were treated with compounds at 10.00 μmol/l; The compound structures are showed in formula 1, wherein 2: $R_1=H$, $R_2=4\text{-Cl}-C_6H_4$, $R_3=R_4=H$; 3; $R_1=H$, $R_2=4\text{-Cl}-C_6H_4$, $R_3=R_4=COR_5$, $R_5=3\text{-pyridine}$; 4: $R_1=H$, $R_2=C_6H_5$, $R_3=R_4=H$; 5: $R_1=H$, $R_2=4\text{-F}-C_6H_4$, $R_3=R_4=H$; 6: $R_1=H$, $R_2=4\text{-Br}-C_6H_4$, $R_3=R_4=H$; 7: $R_1=H$, $R_2=4\text{-CH}_3\text{O}-C_6H_4$, $R_3=R_4=H$; 8: $R_1=H$, $R_2=4\text{-Cl}-C_6H_4$, $R_3=R_4=COR_5$, $R_5=CH_2CH_2COOH$)

Example 3

Inhibition of ECV304 Human Vascular Endothelial Cells 3.1 Materials and Methods

1) Inhibitory Effect on Two-Dimensional Migration of ECV304

The assay procedure of the inhibition of two-dimensional migration of ECV304, which was purchased from China Center for Type Culture Collection (CCTCC, Wuhan, China), was the same with that of tumor cells in EXAMPLE 2.

2) Inhibitory Effect on Three-Dimensional Migration of ECV304

The culture medium without serum was added to the upper and the lower chambers of Transwell chamber, and then it was incubated at 37 for 1 h. ECV304 cells grown to 80-90% confluence were trypsinized and suspended in the culture medium containing 10% fetal bovine serum to adjust the concentration of cells to $1\times10^6$/mL. After the culture medium in the upper and lower of Transwell chamber was taken out, the cell suspension was added into the upper chamber (100 μl/well) while the culture medium containing 10% fetal bovine serum was added into the lower chamber (600 μl/well), then it was cultured at 37 in a humidified atmosphere with 5% $CO_2$. 2 h later, medium in the upper chamber was replaced by serum-free medium with or without drugs, cultured for 18 h. The experiment was performed in triplicate. Cells on the upper surface of the chamber were wiped out with a cotton swab, then the filter membranes were removed, fixed with methanol for 30 min and stained with haematoxylin. Cells that invaded to the lower chamber were counted in five fields of view randomly using a microscope at a magnification of 200×. The average number of cells and the cell migration inhibition ratio (MI %) of drugs were calculated as follows: MI (%)=$(1-Nt/Nc)\times 100\%$; where: Nt—the mean number of migration cells of compound treatment group; Nc—the mean number of migration cells of control group.

3.2 Results

Figure 1A:
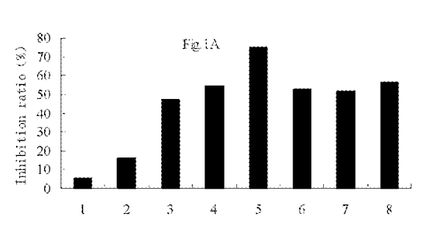
FIG. 1 shows inhibitory effect of compounds 2-8 on the two-dimensional migration of various tumor cells; wherein picture A shows the inhibitory effect on Eca-109 human esophageal carcinoma cells (24 h), picture B shows the inhibitory effect on HT29 human colorectal carcinoma cells (24 h); picture C shows the inhibitory effect on 5637 human urinary bladder cancer cells (24 h); picture D shows the inhibitory effect on SGC-7901 human gastric adenocarcinoma cells (36 h); picture E shows the inhibitory effect on A549 human lung carcinoma cells (36 h); picture F shows the inhibitory effect on PC-3 human prostate carcinoma cells (36 h).
Figure 1B:
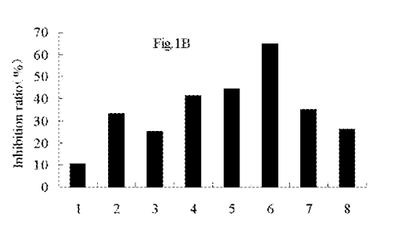
Figure 1C:
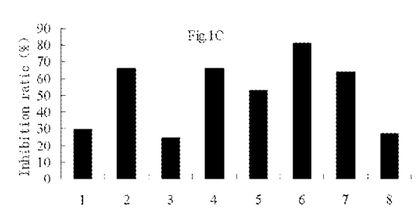
Figure 1D:
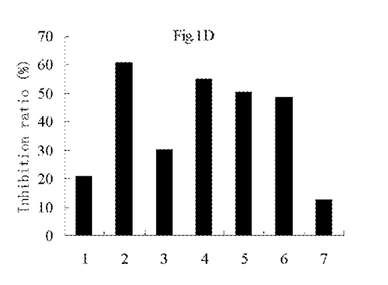
Figure 1E:
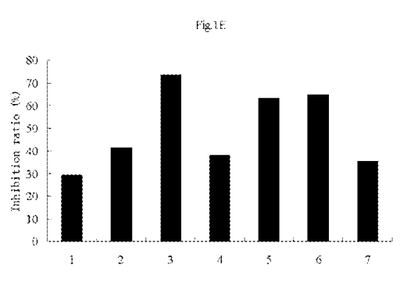
Figure 1F:
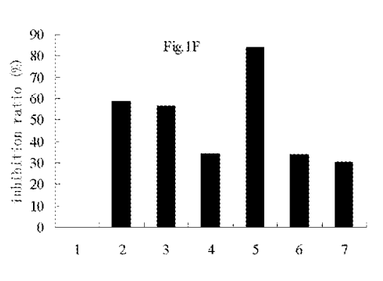
Figure 2A:
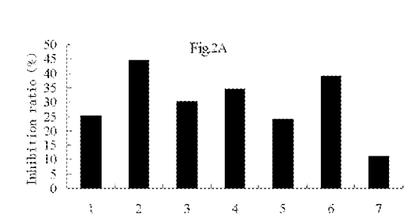
FIG. 2 shows inhibitory effects of compounds 2-8 on the two-dimensional and three-dimensional migration of ECV304 cells; wherein picture A shows the inhibitory effect on the two-dimensional migration; picture B shows the inhibitory effect on the three-dimensional migration.
Figure 2B:
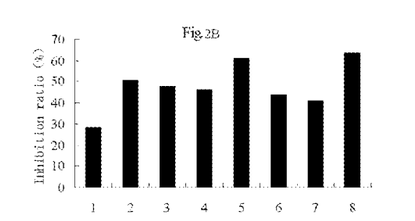

The results of compounds 2-8 on inhibition of two-dimensional and three-dimensional migrations of ECV304 were showed in Fig. A and B of FIG. 2, respectively. It indicated that compounds 2-7 exhibited potent inhibition against two-dimensional migration of ECV304, of which compound 2 was the most significant one. Compounds 2-8 effectively inhibited the three-dimensional migration of ECV304, which were significantly stronger than AD (1).

(Notes for FIG. 2: Results were those when cells were treated with compounds at 10.00 μmol/L. The compound structures are showed in formula 1, wherein 2: $R_1=H$, $R_2=4$-

Cl—$C_6H_4$, $R_3=R_4=H$; 3: $R_1=H$, $R_2=$4-Cl—$C_6H_4$, $R_3=R_4=COR_5$, $R_5=$3-pyridine; 4: $R_1=H$, $R_2=C_6H_5$, $R_3=R_4=H$; 5: $R_1=H$, $R_2=$4-F—$C_6H_4$, $R_3=R_4=H$; 6: $R_1=H$, $R_2=$4-Br—$C_6H_4$, $R_3=R_4=H$; 7: $R_1=H$, $R_2=$4-$CH_3O$—$C_6H_4$, $R_3=R_4=H$; 8: $R_1=H$, $R_2=$4-Cl—$C_6H_4$, $R_3=R_4=COR_5$, $R_5=CH_2CH_2COOH$).

Example 4

Anti-tumor and Anti-Angiogenesis Effects on H22 Tumor-Bearing Mice 4.1 Materials and Methods 1) Animals: Kunming mice of clean grade, half male and half female, body weight 20±2 g, were purchased from the experimental animal center of Henan Province, China. Qualified Certificate number: SCXK (Yu) 2005-0001.

2) Cells: Murine hepatoma H22 cells were presently obtained from Henan Academy of Medical and Pharmaceutical Sciences (Zhengzhou, China).

3) Preparation of Drugs and Reagents

Cyclophosphamide (Cyc) was produced by Tianjin Jingshi Pharmaceutical Co., Ltd., China (approval number of medicine: H12021006). Gelatin and carmine red were supplied by Sigma Chemical (St. Louis, Mo., U.S.A). All other chemicals and reagents were of the highest commercial grade available. All drugs were prepared with normal saline emulsified with Tween-80 (0.1% v/v) and dispersed in carboxymethylcellulose (0.5% v/v). 10% (W/V) carmine solution was prepared with salt solution containing 5% (W/V) gelatin which should be used immediately after preparation. The rest of medicines and reagents and the methods for preparation were the same with that of EXAMPLE 1.

4) Method: The H22 cells after in vivo passage for 7 d were diluted with physiological saline to adjust to a concentration of $1\times10^7$/mL, injected to the armpit of right forelimb of mice subcutaneously (0.2 ml/mouse), then mice were divided into 10 groups (n=12; 6 male and 6 female per group) randomly. 24 h later each group of mice was administrated intragastrically (ig; 0.2 ml/10 g) once a day continuously for 7 d with vehicle (tumor control group and control group), Cyc (standard control), or compounds at the tested doses. After the last drug administration and a following fasting of 8 h, each mouse was anesthetized with 1% pentobarbital in normal saline solution (80 mg/kg; ip). Mice of control group were injected with 5% gelatin in normal saline solution (40) via the tail vein (1 ml/mouse); whereas mice of other groups were injected replaced by 10% carmine red and 5% gelatin in normal saline solution (40). Mice were killed, then freezed in a refrigerator at −20 for 2 h to solidify. Tumors were segregated, weighed and homogenized with 3 M NaOH solution (10 ml/g tumor). The homogenate supernatant was prepared by being centrifuged for 20 min at 14000 rpm, and the absorbance at 490 nm was assayed using a PowerWaveX Microplate Scanning Spectrophotometer (Bio-tek Instruments, Inc). The carmine red content was calculated based on the standard curve. The vascular index (VI) expressed as milligram of carmine red per gram of tumor tissue. The inhibition ratio (IR) of tumor growth was calculated using the formula: IR (%)=[(Wc−Wt)/Wc]×100%, where Wc is the average tumor weight of the control group, and Wt is that of the drug treatment group. Data were expressed as mean±SD and statistical analysis was performed by SPSS Statistics 17.0 using a one-way analysis of variance (ANOVA) followed by unpaired t-test. A value of P<0.05 was considered statistically significant.

4.2 Results

The results about inhibitory effects of andrographolide and two compounds of this invention, compounds 2 and 3, on tumor growth were shown in Table 2. The results showed that tumors in mice treated (ig) with andrographolide (1) at 1.35 mmol/kg or Cyc at 20 mg/kg shrank significantly compared with that in mice of tumor control group (P<0.05). Compared with compound 1 (1.35 mmol/kg), the inhibitory effects on growth of mouse hepatoma H22 remarkably enhanced by compounds 2 and 3, in a dose-dependent manner (P<0.01). The VI value of mice administrated with Cyc at 20 mg/kg and compound 1 (1.35 mmol/kg) significantly decreased, compared with that of mice treated with vehicle. Compound 3 at the dose of 0.65 mmol/kg, 1.00 mmol/kg, or 1.35 mmol/kg could reduce the VI values of tumor tissues in mice with different degrees, of which the antiangiogenesis by compound 3 at 1.00 mmol/kg was stronger than that at 0.65 mmol/kg and 1.35 mmol/kg. The VI value in mice treated with compound 2 declined in a dose-dependent manner. Therefore, the compounds 2 and 3 had significant inhibition against the growth of mouse hepatoma H22 as well as the angiogenesis.

TABLE 2

The effects of andrographolide and compounds of this invention, 2 and 3, on tumor growth and angiogenesis ($\bar{x} \pm s$)

| Group | Dose | IR (%) | Carmine contents | VI (mg/g) |
|---|---|---|---|---|
| Tumor control | / | / | 5.52 ± 3.94 | 4.82 ± 2.43 |
| Cyc | 20.00 mg/kg | 29.34* | 4.24 ± 2.29 | 4.87 ± 1.13 |
| Compound 1 | 1.35 mmol/kg | 31.70* | 4.66 ± 2.58 | 5.10 ± 2.13 |
| Compound 3 | 0.65 mmol/kg | 37.89* | 2.26 ± 1.97*$^\Delta$ | 3.60 ± 1.86*$^\Delta$ |
| Compound 3 | 1.00 mmol/kg | 41.26*$^{\Delta\Delta}$ | 1.88 ± 1.26**$^{\Delta\Delta}$ | 3.30 ± 1.43*$^\Delta$ |
| Compound 3 | 1.35 mmol/kg | 49.27**$^{\Delta\Delta}$ | 2.14 ± 1.42*$^\Delta$ | 3.88 ± 1.40 |
| Compound 2 | 0.65 mmol/kg | 15.69 | 4.63 ± 2.93 | 4.42 ± 1.58 |
| Compound 2 | 1.00 mmol/kg | 49.63**$^{\Delta\Delta}$ | 2.59 ± 1.68*$^\Delta$ | 3.89 ± 0.89 |
| Compound 2 | 1.35 mmol/kg | 50.37**$^{\Delta\Delta}$ | 1.90 ± 1.39**$^{\Delta\Delta}$ | 3.14 ± 1.69*$^\Delta$ |

Compared with the tumor control group:
*P < 0.05,
**P < 0.01;
compared with the compound 1 group:
$^\Delta$P < 0.05,
$^{\Delta\Delta}$P < 0.01

Example 5

Inhibition on the Growth, Invasion and Metastasis of S180 Sarcoma in the Tumor-Bearing Mice 5.1 Materials and Methods 1) Animals: Be the same with that of EXAMPLE 4.
2) Cells: The S180 murine sarcoma cells were obtained from Henan Academy of Medical and Pharmaceutical Sciences (Zhengzhou, China).
3) Preparation of drugs and reagents: Be the same with that of EXAMPLE 4.
4) Method: Mice were randomly divided into 10 groups (n=12). The S180 cells after in vivo passage for 7 d were diluted with physiological saline to adjust to a concentration of $1\times10^7$/mL. The inoculation of tumor cells was conducted in two batches, those of tumor control group I and groups treated with compounds 1 or 3 were in batch 1, those of tumor control group II, Cyc group and the compound 2 groups were in batch 2. The mice were injected with S180 cells (0.2 ml/mouse) into the armpit of right forelimb subcutaneously, and 24 h later each group of mice was administrated intragastrically (ig; 0.2 ml/10 g) once a day continuously for 9 d with vehicle (tumor control group), Cyc (standard control), or compounds at the tested doses. On day 10, kill the mice, observe and record the degree of invasion and metastasis of tumor tissues, then the tumor tissues were segregated and weighed. The inhibition ratio (IR) of tumor growth was calculated by the following formula: IR (%)=[(Wc−Wt)/Wc]×100%, where Wc is the average tumor weight of the control group, and Wt is that of the treatment group. Data were expressed as mean±SD and statistical analysis was performed by SPSS Statistics 17.0 using a one-way analysis of variance (ANOVA) followed by unpaired t-test. A value of P<0.05 was considered statistically significant.

5.2 Results

As shown in Table 3, the mean weight of sarcoma S180 in mice was remarkably decreased by Cyc (P<0.01), and the inhibition ratio was 53.61% at dose of 30 mg/kg. Andrographolide and compounds of this invention, 2 and 3, could significantly inhibit the tumor growth in the tested dose range. Compared with that treated with andrographolide, the mean weights of sarcoma in mice administrated with compound 2 at 0.85 mmol/kg (P<0.01), 1.10 mmol/kg (P<0.05), compound 3 at 1.35 mmol/kg (P<0.05) were significantly lowered. Therefore, it is obvious that the in vivo antitumor effects of compounds 2 and 3 are significantly stronger than that of the parent compound, and the inhibition of compound 2 is stronger than that of compound 3.

TABLE 3

Inhibition of the present compounds against growth of S180 sarcoma

| Group | Dose | IR (%) |
|---|---|---|
| Tumor control I | / | / |
| Compound 1 | 1.35 mmol/kg | 17.18 ± 3.21* |
| Compound 3 | 0.60 mmol/kg | 18.89 ± 3.68* |
| Compound 3 | 0.85 mmol/kg | 20.21 ± 4.37* |
| Compound 3 | 1.10 mmol/kg | 24.44 ± 6.30** |
| Compound 3 | 1.35 mmol/kg | 31.21 ± 5.96**Δ |
| Tumor control II | / | / |
| Cyc | 30.00 mg/kg | 53.61 ± 12.43** |
| Compound 2 | 0.60 mmol/kg | 30.12 ± 8.00** |
| Compound 2 | 0.85 mmol/kg | 53.38 ± 6.83**ΔΔ |
| Compound 2 | 1.10 mmol/kg | 45.16 ± 5.58**ΔΔ |

Compared with the model group:
*P < 0.05,
**P < 0.01;
compared with the group treated with compound 1:
ΔP < 0.05,
ΔΔP < 0.01

The grading method was used to evaluate the effect of compounds on tissue invasion and metastasis of S180 sarcoma (Table 4). The results showed that compounds of this invention, 2 and 3, exhibited strong inhibitory effect on invasion and metastasis of tumor tissues.

TABLE 4

Inhibitory effect of compounds of this invention on invasion and metastasis of S180 sarcoma

| Group | Dose | Mouse Number | | | | | |
|---|---|---|---|---|---|---|---|
| | | Grade 0 | Grade 1 | Grade 2 | Grade 3 | Grade 4 | Average |
| Model I | / | 0 | 0 | 2 | 9 | 0 | 2.80* |
| 1 | 1.35 mmol/kg | 6 | 4 | 2 | 0 | 0 | 0.67 |
| 3 | 0.60 mmol/kg | 4 | 5 | 1 | 2 | 0 | 1.08 |
| 3 | 0.85 mmol/kg | 5 | 2 | 2 | 3 | 0 | 1.25 |
| 3 | 1.10 mmol/g | 8 | 3 | 1 | 0 | 0 | 0.42 |
| Model II | / | 0 | 0 | 1 | 2 | 9 | 3.75 |
| Cvc | 30.00 mg/kg | 0 | 0 | 0 | 4 | 8 | 3.67 |
| 2 | 0.60 mmol/kg | 0 | 0 | 12 | 0 | 0 | 2.00 |
| 2 | 0.85 mmol/kg | 12 | 0 | 0 | 0 | 0 | 0.00 |
| 2 | 1.10 mmol/kg | 12 | 0 | 0 | 0 | 0 | 0.00 |

*One mouse have died before the end of experiment;
Grade 0: no invasion; Grade 1: invasion to right forelimb; Grade 2: invasion to right forelimb and the left side of body; Grade 3: invasion to right forelimb, the left side of body, and also the ribs and muscles in chest; Grade 4: invasion into chest or abdominal cavity.

Example 6

Inhibitory Effect of Compound 3 on Experimental Lung Metastasis 6.1 Materials and Methods 1) Animals: A total of 20 C57BL/6 male mice of clean grade [Number of Animal License: SCXK (Xiang) 2009-

0004], weighing 18-22 g, were purchased from Hunan Slca Jingda Experimental Animal Center Company, Ltd., China.

2) Cells: B16-F10 mouse melanoma cells were purchased from Nanjing KeyGen Biotech. Co. Ltd., China.

3) Drugs and reagents: Mouse tumor necrosis factor-α (TNF-α) ELISA kit (EK 0527), mouse interleukin-1β (IL-1β) ELISA kit (EK0394) were purchased from Wuhan Boster Biological Engineering Co. Ltd., China. Other drugs and the preparation of drugs were the same with EXAMPLE 4.

4) Method: B16-F10 cells in logarithmic growth phase were trypsinized, then resuspended in RPMI1640 medium containing 10% fetal bovine serum and centrifuged at 1000 rpm for 5 min. The supernatant was removed and sterile PBS was added to prepare single-cell suspension ($10^7$/mL). The murine melanoma lung metastasis model was established in mice via caudal vein injection of B16-F10 cells (0.2 ml/mouse). Mice were randomly divided into 4 groups (n=5) according to body weight, and 24 h later they were administrated intragastrically (ig; 0.2 ml/10 g) once a day continuously for 24 d with vehicle (tumor control group), Cyc (30 mg/kg), compound 3 at 0.85 mmol/kg and 1.10 mmol/kg. Mice were weighed and blood was collected by removing the eyeball at 24 h after the last administration. Sacrificed the mice, removed the lung and counted the number of melanoma nodules in lungs of mice under an anatomical lens. Serum obtained after centrifugation at 3000 rpm for 20 min (3K30 refrigerated centrifuge, Sigma, USA) was conserved at $-20°$ C. Levels of TNF-α and IL-1β in serum were measured by ELISA method, which were performed in accordance with the instructions of the kits.

Data were expressed as mean±SD and statistical analysis was performed by SPSS Statistics 17.0 using a one-way analysis of variance (ANOVA) followed by unpaired t-test. A value of $P<0.05$ was considered statistically significant. The inhibition ratio (IR %) of lung metastasis was calculated as follows: IR %=(Nc−Nt)/Nc×100%, where Nc is the average number of nodules in lung tissues of vehicle, and Nt is that of mice treated with drugs.

6.2 Results

Showed by the statistical results (Table 5), the number of nodules in lung surface of mice administrated with compound 3 at low and high-dose, and Cyc with the inhibition ratio 58.04%, 65.18%, 47.92%, respectively, was significantly lower than that with vehicle ($P<0.01$). Compound 3 at 1.10 mmol/kg (ig) showed the strongest inhibitory effect, which was significantly stronger than that of Cyc ($P<0.05$).

TABLE 5

Inhibitory effect of compound 3 on lung metastasis of B16-F10 mouse melanoma ($\bar{x} \pm s$; n = 5)

| Group | Concentration | Lung index (mg/g) | Nodule number | IR (%) |
|---|---|---|---|---|
| Tumor control | / | 6.29 ± 1.01 | 84.00 ± 8.76 | / |
| Cyc | 30.00 mg/kg | 6.66 ± 0.37 | 43.76 ± 11.70** | 47.92% |
| Compound 3 | 0.85 mmol/kg | 6.19 ± 0.76 | 35.25 ± 14.45** | 58.04% |
|  | 1.10 mmol/kg | 6.39 ± 0.57 | 29.25 ± 881**V | 65.18% |

Compared with model group:
**$P < 0.01$;
compared with cyclophosphamide:
V$P < 0.05$.

Figure 3:
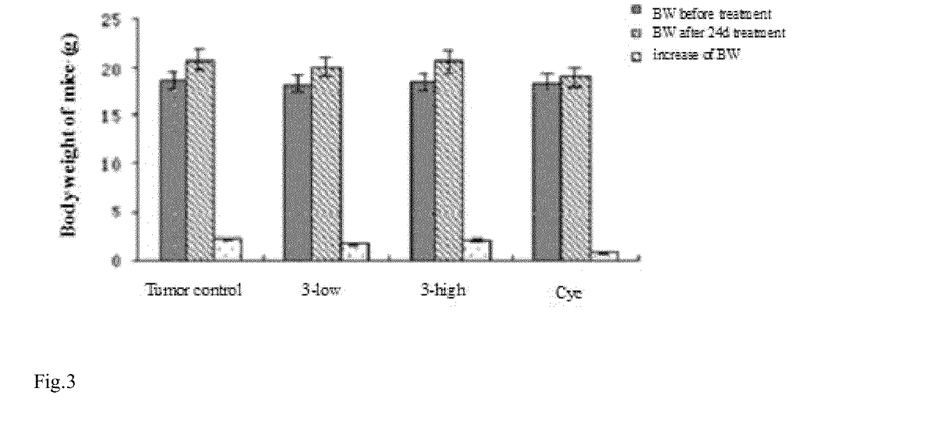
FIG. 3 shows the changes in mean body weight of C57BL/6 mice in each group, before and 24 d after administration.

Compared with the changes in body weight (BW) of each group of C57BL/6 mice before and 24 d after the administration (FIG. 3), the increase in body weight of the mice treated with Cyc was the minimum (the average value is equal to 0.7 g) which was lower than that treated with vehicle (the average value is equal to 2.1 g), but the difference did not reach a significant level ($P>0.05$). The average net increase in body weight of mice administrated with compound 3 at 0.85 mmol/kg and 1.10 mmol/kg were 1.64 g and 2.00 g, respectively, which were of no statistical significance compared with that of mice in model group ($P>0.05$).

Levels of TNF-α and IL-1β in mouse serum were showed in Table 6. Compound 3 at dose of 0.85 mmol/kg or 1.10 mmol/kg down-regulated the expression of IL-1β in serum, of which that of the high-dose group reached a significant level ($P<0.05$), compared with that of mice treated by vehicle. Compound 3 at 0.85 mmol/kg significantly inhibited the expression of TNF-α in serum, which was considered to be statistically significant compared with that of mice in model group ($P<0.05$).

TABLE 6

Effect of compound 3 on the levels of TNF-α and IL-1β in the serum of C57BL/6 mice ($\bar{x} \pm s$; n = 5)

| Group | Dose | IL-1β (pg/mL) | TNF-α |
|---|---|---|---|
| Tumor | / | 41.58 ± 14.00 | 11.76 ± 4.96 |
| Cyc | 30.00 mg/kg | 41.58 ± 4.39 | 8.45 ± 9.54 |
| Compound 3 | 0.85 mmol/kg | 30.76 ± 3.25 | 0.52 ± 5.90* |
|  | 1.10 mmol/kg | 17.86 ± 3.41* | 11.11 ± 5.96 |

Compared with model group,
*$P < 0.05$.

Example 7

The Acute Oral Toxicity Test

Maximum Limit Method 7.1 Materials and Methods

1) Animals: Be the same with that of EXAMPLE 4.
2) Drugs: Compounds of this invention, 2 and 3.
3) Method: 20 mice weighing 20±2 g, half male and half female, were divided into 2 groups (n=10) randomly. Animals were administrated with compound 2 or compound 3 at a dose of 5.00 g/kg by intragastric administration after 12 h of fasting (drinking freely). Weigh the mice, observe and record the performance of animals once a day continuously for 14 d. Results were shown in Table 7.

7.2 Results

No apparent toxic symptoms were observed in mice after treated with the tested compound and no mouse died in the period of experiment, which suggested that compounds 2 and 3 are of minimal cytotoxicity. Therefore, it was of high practical value of compounds of this invention for preparing anti-cancer drugs.

TABLE 7

Acute toxicity test of compounds 2 and 3

| Compound | Dose (g/kg) | Animal | Deaths | Mortality(%) |
|---|---|---|---|---|
| 2 | 5.00 | 10 | 0 | 0 |
| 3 | 5.00 | 10 | 0 | 0 |

In summary, the derivatives of this kind were of exact anti-tumor activity, efficiency and low toxicity, which had the potential to be developed as anti-tumor drugs used for the treatment and prevention of metastasis of tumor.

The compound numbers used in the experiments were consistent. Compound 1 is andrographolide, compounds 2-8 are the compounds of present invention.

What is claimed is:

1. A method of treating cancer in a subject in need thereof, comprising administering an andrographolide derivative of Formula 1, Formula 1 wherein $R_1$ is hydrogen;
$R_2$ is phenyl, or halophenyl; and
$R_3$ and $R_4$ are each independently hydrogen, and
wherein the cancer is at least one of gastric cancer, esophageal cancer, colon cancer, or liver cancer.

2. The method of claim 1, wherein $R_2$ is phenyl, p-fluorophenyl, p-chlorophenyl, p-bromophenyl, 3-fluorophenyl, 3-chlorophenyl or 3-bromophenyl.

3. The method of claim 1, wherein $R_2$ is p-chlorophenyl.

4. The method of claim 1, wherein the andrographolide derivative of Formula 1 is in an oral or injectable pharmaceutical preparation.

5. The method of claim 4, wherein the oral preparation is a tablet, pill, capsule, granule or syrup; and the injectable preparation is an injectable liquid or a lyophilized powder for injection.

6. A method of treating gastric cancer in a subject in need thereof, comprising administering an andrographolide derivative of Formula 1, Formula 1 wherein $R_1$ is hydrogen;
$R_2$ is halophenyl; and
$R_3$ and $R_4$ are each independently hydrogen.

7. The method of claim 6, wherein $R_2$ is p-fluorophenyl, p-chlorophenyl, or p-bromophenyl.

8. The method of claim 6, wherein $R_2$ is p-fluorophenyl.

9. The method of claim 6, wherein $R_2$ is p-chlorophenyl.

10. The method of claim 6, wherein $R_2$ is p-bromophenyl.

* * * * *

UNITED STATES PATENT AND TRADEMARK OFFICE
CERTIFICATE OF CORRECTION

PATENT NO. : 9,198,894 B2  
APPLICATION NO. : 13/823841  
DATED : December 1, 2015  
INVENTOR(S) : Guifu Dai et al.

Page 1 of 1

It is certified that error appears in the above-identified patent and that said Letters Patent is hereby corrected as shown below:

Title Page,

Item (12), Delete "Wu et al." and insert --Dai et al.--

Item (75), Inventors:

Delete "Fengjuan Wu (Zhengzhou, CN); Guifu Dai (Zhengzhou, CN); Haiwei Xu (Zhengzhou, CN); Liping Zhu (Zhengzhou, CN); Lijun Yan (Zhengzhou, CN); Hongmin Liu (Zhengzhou, CN); Yanan Wang (Zhenghzou, CN); Weiyi Li (Zhengzhou, CN); Rujing Dong (Zhengzhou, CN)"

Insert --Guifu Dai (Zhengzhou, CN); Haiwei Xu (Zhengzhou, CN); Liping Zhu (Zhengzhou, CN); Ruijing Dong (Zhengzhou, CN); Fengjuan Wu (Zhengzhou, CN); Yanan Wang (Zhengzhou, CN); Zhiwen Jiang (Zhengzhou, CN); Lijun Yan (Zhengzhou, CN); Weiyi Li (Zhengzhou, CN); Hongmin Liu (Zhengzhou, CN)--

Signed and Sealed this  
Fifth Day of July, 2016

Michelle K. Lee  
*Director of the United States Patent and Trademark Office*